(12) United States Patent
Krasnow et al.

(10) Patent No.: US 11,852,625 B1
(45) Date of Patent: Dec. 26, 2023

(54) SYSTEMS AND METHODS FOR ANALYZING EXHALED BREATH

(71) Applicant: Verily Life Sciences LLC, South San Francisco, CA (US)

(72) Inventors: Benjamin Krasnow, Redwood City, CA (US); Eric Peeters, Redwood City, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 496 days.

(21) Appl. No.: 16/849,733

(22) Filed: Apr. 15, 2020

Related U.S. Application Data

(60) Provisional application No. 62/834,456, filed on Apr. 16, 2019.

(51) Int. Cl.
*G01N 33/497* (2006.01)
*A61B 5/097* (2006.01)
*A61B 5/08* (2006.01)
*G01N 31/22* (2006.01)

(52) U.S. Cl.
CPC .......... *G01N 33/497* (2013.01); *A61B 5/082* (2013.01); *A61B 5/097* (2013.01); *G01N 31/223* (2013.01)

(58) Field of Classification Search
CPC .... G01N 33/497; G01N 31/223; A61B 5/082; A61B 5/097
See application file for complete search history.

(56) References Cited

U.S. PATENT DOCUMENTS

| | | | | |
|---|---|---|---|---|
| 9,643,186 | B1* | 5/2017 | Ahmad | B01L 3/52 |
| 2016/0202225 | A1* | 7/2016 | Feng | G01N 29/022 |
| | | | | 422/90 |
| 2016/0371590 | A1* | 12/2016 | Blackley | G01N 33/497 |
| 2017/0119279 | A1* | 5/2017 | Ahmad | A61B 5/082 |
| 2017/0224251 | A1* | 8/2017 | Ahmad | A61B 5/087 |
| 2018/0056302 | A1* | 3/2018 | Ahmad | G01N 33/542 |
| 2019/0231222 | A1* | 8/2019 | Ahmad | A61B 5/091 |
| 2019/0261891 | A1* | 8/2019 | Ahmad | A61B 5/087 |
| 2021/0059560 | A1* | 3/2021 | Allegra | A61B 5/4839 |

* cited by examiner

*Primary Examiner* — Orlando Bousono
(74) *Attorney, Agent, or Firm* — Kilpatrick Townsend & Stockton LLP

(57) ABSTRACT

Described herein are systems and methods of collecting, processing, and analyzing breath exhaled from a subject. Specifically, described herein are systems and methods for minimizing the amount of breath needed for analysis. Further disclosed herein are systems and methods to analyze compounds contained in a subject's breath that are indicative of certain ailments and/or present in a low concentration in the subject's breath. The systems can include a reaction chamber, a breath inlet, a reactant inlet, a fluid atomizer, and a receiving substrate for analyzing the process subject's breath. The methods can include reacting a subject's breath with a reactant to analyze the contents of the subject's breath.

24 Claims, 1 Drawing Sheet

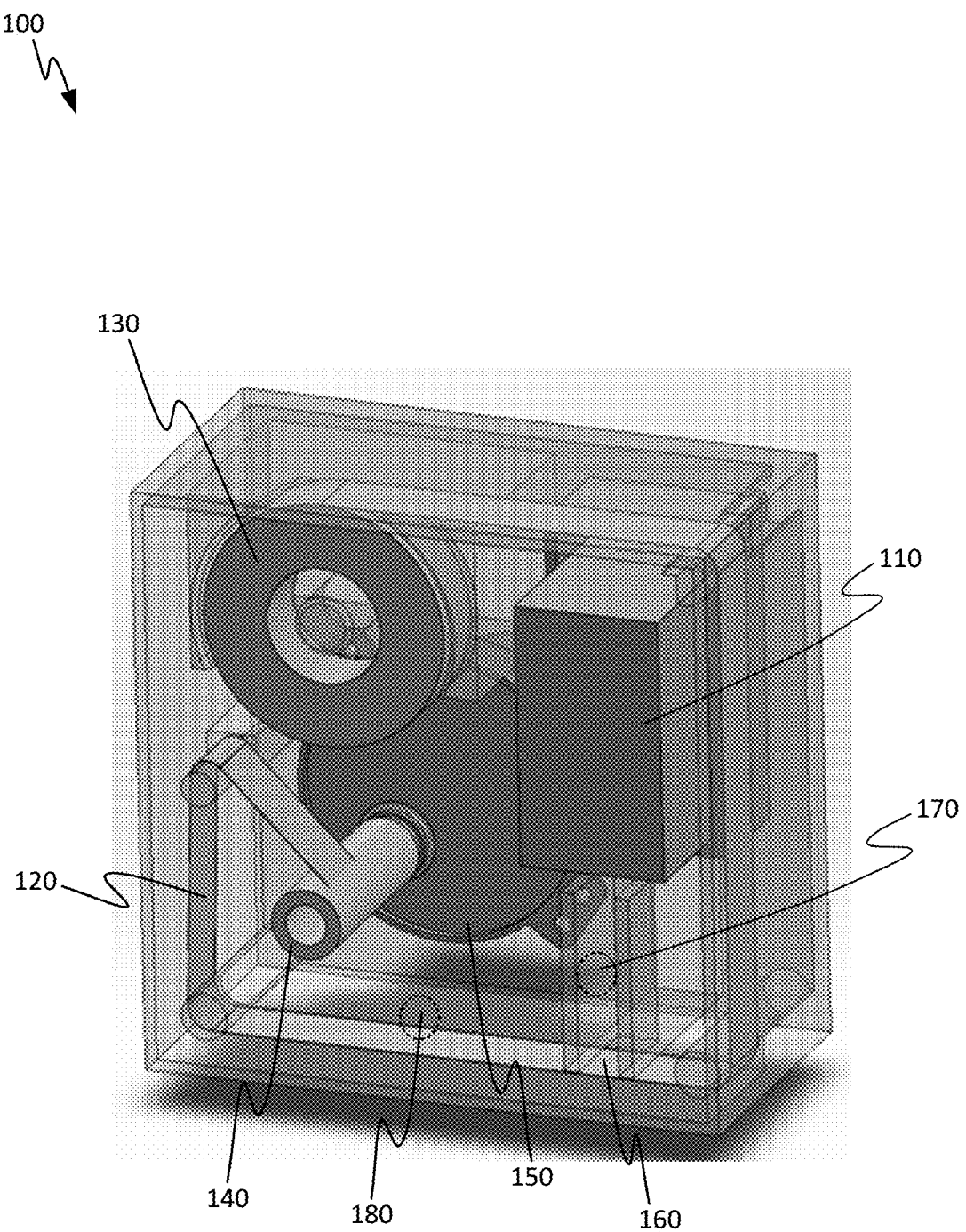

SYSTEMS AND METHODS FOR ANALYZING EXHALED BREATH

CROSS-REFERENCE TO RELATED APPLICATIONS

This application claims priority under 35 U.S.C. § 119 to U.S. Provisional Patent Application No. 62/834,456, filed on Apr. 16, 2019, the contents of which are hereby incorporated by reference in their entirety.

BACKGROUND

Exhaled breath is a biological sample that can be used as a non-invasive source of analytes. Analyzing the contents of a subject's exhaled breath for biomedical analysis, in fact, is an active area of development. However, systems to date require large amounts of the subject's breath for meaningful assessment and acquisition of such large samples can be problematic if the subject is uncooperative or if the subject has a compromised pulmonary system.

SUMMARY

Disclosed herein is a highly sensitive breath analysis system that is effective for small breath sample sizes. Such systems for analyzing a subject's breath comprise a breath inlet configured to receive the subject's breath; a reaction chamber comprising a receiving substrate, wherein the receiving substrate is positioned inside the reaction chamber and is configured to receive a reaction product from a reaction between the subject's breath and an indicator fluid and wherein the reaction chamber is in fluid communication with the breath inlet and configured to receive the subject's breath through the breath inlet; a nozzle comprising a delivery end positioned at or within the reaction chamber and a supply end positioned outside the reaction chamber, wherein the nozzle is configured to receive an indicator fluid at its supply end and to dispense the indicator fluid into the reaction chamber; and an indicator fluid delivery device in fluid communication with the supply end of the nozzle.

In certain embodiments, the system includes an indicator fluid storage vessel in fluid communication with the indicator fluid delivery device. In some cases, the system includes a sensor configured to analyze the reaction product. In certain aspects, the sensor comprises an optical sensor, and/or a chemical sensor capable of detecting and/or quantifying one or more reaction products. In some cases, the reaction chamber comprises a chamber volume of up to about 10 milliliters, preferably up to about 5 milliliters. The nozzle is optionally configured to dispense the indicator fluid as an atomized fluid, an aerosol, or a liquid. In certain embodiments, the indicator fluid is an atomized fluid comprising a plurality of droplets, wherein each droplet in the plurality of droplets comprises an indicator fluid volume of less than one nanoliter (i.e., a sub-nanoliter volume), preferably less than one picoliter (i.e., a sub-picoliter volume).

In certain aspects, the nozzle is configured to dispense the indicator fluid as a liquid and the reaction chamber comprises a piezoelectric disc actuator configured to convert the liquid into a plurality of droplets. The droplets are configured to maximize a reactable surface area of the fluid. By way of example, the plurality of droplets of indicator fluid comprises a reactable surface area of at least about 2000 square centimeters per gram ($cm^2/g$) of indicator fluid. The reactable surface area is optionally at least about 2500 $cm^2/g$ of indicator fluid. In certain embodiments, the nozzle is configured to dispense up to about 100 microliters of the indicator fluid into the reaction chamber for each breath to be analyzed. For example, the nozzle is optionally configured to dispense up to about 50 microliters of the indicator fluid into the reaction chamber for each breath to be analyzed.

In some examples, the reaction chamber is configured to receive up to about 100 milliliters of the subject's breath or a selected volume of less than 100 milliliters. For example, the reaction chamber is optionally configured to receive about 50 milliliters of the subject's breath. In some cases, the reaction chamber is configured to receive up to about 8 liters per minute of the subject's breath (e.g., up to about 5 liters per minute of the subject's breath, or up to about 1 liter per minute of the subject's breath). In some cases, the reaction product comprises a detectable change in color. Additionally, the receiving substrate is optionally configured to optically enhance the visibility or detectability of the reaction product.

Also disclosed herein are methods of analyzing one or more compounds in a subject's breath using the systems described herein. The method includes receiving the subject's breath in the reaction chamber; dispensing one or more indicator fluids into the reaction chamber; reacting the subject's breath with a plurality of droplets of the one or more indicator fluids to produce one or more reaction products on the receiving substrate; detecting the presence or amount of one or more reaction products. In certain embodiments, the detection comprises optical detection, chemical detection, thermal detection, infrared (IR) detection, or any combination thereof.

This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings, and each claim.

BRIEF DESCRIPTION OF THE DRAWINGS

FIG. 1 is a schematic depicting a breath analysis system according to embodiments of the present disclosure.

In the following detailed description, reference is made to the accompanying FIGURES, which form a part hereof. In the FIGURES, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the FIGURES, can be arranged, substituted, combined, separated, and designed in a wide variety of different configurations, all of which are explicitly contemplated herein.

DETAILED DESCRIPTION

Certain aspects and features of the present disclosure relate to analyzing a subject's breath. Specifically, certain aspects and features of the present disclosure relate to detecting and/or measuring analytes in a small breath sample. Additionally, certain aspects and features of the present disclosure relate to analyzing one or more components of a subject's breath present in small amounts (i.e., very low concentrations) in a sample of breath. Subjects with compromised pulmonary function, for example, a subject having asthma or chronic obstructive pulmonary disease (COPD), can undergo a breath analysis requiring a small amount of the exhaled breath. Thus, the disclosed system provides more opportunity for clinical usefulness. Further, certain aspects and features of the present disclosure relate to reacting the components of the subject's breath with selected indicator compositions, such that specific components of the subject's breath can be detected and characterized.

Other objects, advantages and features of the present disclosure will become apparent from the following specification taken in conjunction with the accompanying drawings.

Systems

Disclosed herein are systems for analyzing a subject's breath (e.g., a sample of the subject's exhaled breath). In certain embodiments, the systems are portable systems (e.g., for emergency use, home use, or point-of-care use). In some cases, the systems are integrated into a hospital room, an ambulance, an urgent care facility, or any suitable care facility). In certain non-limiting examples, the systems include at least a reaction chamber, a breath inlet, a nozzle for delivering a fluid reactant into the reaction chamber, and a substrate for capturing and analyzing a reaction product created when the subject's breath reacts with the fluid reactant (e.g., the indicator fluid).

The breath inlet is configured to receive the subject's breath and can be, for example, a tube, a mask, a nipple, a straw, or any apparatus suitable for capturing the subject's breath and providing the subject's breath to the reaction chamber. The breath inlet is optionally a removable and/or interchangeable part that can be replaced to analyze the breath of multiple subjects using a single reaction chamber. Accordingly, the breath inlet can be attached to the reaction chamber by any suitable means, including screw threading, reverse screw-threading, quick-connecting, snap-connecting, twist-locking, latching, clipping, or any suitable attachment means. The breath inlet is configured to capture the subject's breath and relay the captured breath into the reaction chamber. In some cases, the breath inlet includes a valve configured to enclose the subject's breath within the reaction chamber. For example, the valve can be a ball valve, a gate valve, a membrane, a relief valve, or any suitable controllable sealing mechanism.

In certain aspects, the breath inlet is configured to control or limit the volume of the subject's breath that enters the reaction chamber. Accordingly, the volume of the subject's breath that enters the reaction chamber is reduced so as to provide a subunit of the exhaled breath. The volume of breath reaching the reaction chamber is less than the volume required in known breath analysis systems. In some cases, the breath inlet is in fluid communication with a reducing coupling configured to reduce the volume of the subject's breath and to relay the subject's breath into the reaction chamber.

In certain embodiments, the reaction chamber is a chamber in which a chemical reaction and/or the reaction product is observable. For example, the reaction chamber can be constructed, in whole or in part, of a transparent material or a translucent material. In some examples, the reaction chamber is an opaque chamber having a view port configured to provide visual observation of the chemical reaction and/or reaction product. The reaction chamber is constructed of a material that is chemically inert to the subject's breath, the reactant, and the reaction product. Optionally, the reaction chamber is configured to be cleaned or sterilized and re-used. For example, the reaction chamber can be constructed, in whole or in part, of a transparent polystyrene, polycarbonate, poly(methyl methacrylate), polyethylene terephthalate, polyvinyl chloride, polyethylene, polypropylene, acrylonitrile butadiene-styrene, glass, or any suitable transparent or translucent material.

In some cases, the reaction chamber comprises a chamber volume of up to about 10 milliliters (mL), up to about 5 mL, or any amount from 10 to 5 mL or less than 5 mL. For example, the reaction chamber can have a volume of about 10 mL, about 9 mL, about 8 mL, about 7 mL, about 6 mL, or about 5 mL. In certain embodiments, the system requires up to about 10 mL of the subject's breath (e.g., about 1 mL to about 9 mL, about 1 mL to about 8 mL, about 1 mL to about 7 mL, about 1 mL to about 6 mL, about 1 mL to about 5 mL, about 2 mL to about 8 mL, about 3 mL to about 7 mL, or about 4 mL to about 6 mL). Thus, the system can require at least about 10 mL, about 9 mL, about 8 mL, about 7 mL, about 6 mL, about 5 mL, about 4 mL, about 3 mL, about 2 mL, or about 1 mL of a subject's breath. When compared to conventional breath analysis systems requiring up to about 600 mL of a subject's breath, the systems and methods described herein require about 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of the volume of a subject's breath compared to a conventional breath analysis system described above. The systems described herein are especially advantageous for analyzing the breath of subjects with compromised respiratory function (e.g., with COPD, asthma, paralysis, emphysema, respiratory tract infection, post-surgical lung resection, etc.), an unconscious or unresponsive subject, or a child. In some cases the reaction chamber is a portion of a portable device. In some other cases, the reaction chamber is a portion of a system installed in a home, a hospital room, an ambulance, an urgent care facility, or the like).

In certain embodiments, the reaction chamber contains a receiving substrate configured to receive the reaction product from a reaction between the subject's breath and an indicator fluid or an atomized droplets thereof. In certain cases, the receiving substrate is configured to receive the indicator fluid such that the reaction can occur on the receiving substrate. In some examples, the receiving substrate is configured to enhance the visibility of the reaction product. For example, the receiving substrate can be white if the desired reaction product is a color other than white and/or transparent (e.g., when the reaction product is, for example, a translucent yellow material, though it can be any color and have any degree of translucency that is accentuated by the receiving substrate). In some cases, when the reaction occurs on the receiving substrate, the receiving substrate is configured to enhance the visibility of the reaction (e.g., where the reaction produces a color change, an exothermic reaction, an endothermic reaction, a photometric reaction, a light transmission, a light absorption, a change of light emission, or a phase change). In certain embodiments, the receiving substrate is a portion of the reaction chamber. For example, a transparent reaction chamber can have a portion that is an opaque white portion configured to capture the reaction product and/or the indicator fluid. In other embodiments, the receiving substrate is a removable and/or interchangeable part that can be removed for maintenance or replacement.

By way of example, the receiving substrate can be a tape or a slide. For example, the receiving substrate can be a transparent tape, a translucent tape, an opaque tape, a transparent slide, a translucent slide, or an opaque slide. The receiving substrate optionally includes a receiving side and a non-receiving side. Optionally, the sensor can be positioned to read the receiving side of the receiving substrate. In some cases, in the example of a transparent receiving substrate, the sensor can be positioned to read the non-receiving side of the substrate. In certain aspects the receiving substrate is a static substrate or the receiving substrate can be a moveable substrate.

In certain embodiments, the receiving substrate is a moveable substrate configured to carry the reaction product from a reaction site (e.g., a position in the reaction chamber adjacent to the indicator fluid dispensing nozzle) to a sensor configured to characterize the reaction product. Accordingly, the reaction chamber can be positioned at a first location and the receiving substrate can be configured to pass through the reaction chamber. The moveable receiving substrate can be configured to capture the reaction product and carry the reaction product to a position adjacent to the sensor (e.g., an optical sensor, a spectrophotometer, a fluorescence spectrometer, an absorption spectrometer, a camera, or any suitable visible light detector, a chemical sensor, an infrared (IR) detector, or any sensor suited to detect the desired chemical reaction product). As such, the sensor need not be positioned within the reaction chamber. In the example of a color change reaction, a visible light sensor can detect the color of the reaction product. In the example of an exothermic or endothermic reaction, an IR detector can detect a temperature or a temperature change.

In certain embodiments, the system includes at least a nozzle having a delivery end positioned at or within the reaction chamber and a supply end positioned outside of the reaction chamber, wherein the nozzle is configured to receive the indicator fluid at its supply end and to dispense the indicator fluid into the reaction chamber at the delivery end of the nozzle. In certain aspects, the system further includes an indicator fluid delivery device in fluid communication with the supply end of the nozzle. In some examples, the nozzle is configured to atomize the indicator fluid. As described herein, an atomized fluid is a fluid delivered as a plurality of droplets having a volume of from about 10 femtoliters (fL) to about 1 nanoliter (nL). For example, the droplets can have a volume of about 10 fL, about 20 fL, about 30 fL, about 40 fL, about 50 fL, about 60 fL, about 70 fL, about 80 fL, about 90 fL, about 100 fL, about 110 fL, about 120 fL, about 130 fL, about 140 fL, about 150 fL, about 160 fL, about 170 fL, about 180 fL, about 190 fL, about 200 fL, about 210 fL, about 220 fL, about 230 fL, about 240 fL, about 250 fL, about 260 fL, about 270 fL, about 280 fL, about 290 fL, about 300 fL, about 310 fL, about 320 fL, about 330 fL, about 340 fL, about 350 fL, about 360 fL, about 370 fL, about 380 fL, about 390 fL, about 400 fL, about 410 fL, about 420 fL, about 430 fL, about 440 fL, about 450 fL, about 460 fL, about 470 fL, about 480 fL, about 490 fL, about 500 fL, about 510 fL, about 520 fL, about 530 fL, about 540 fL, about 550 fL, about 560 fL, about 570 fL, about 580 fL, about 590 fL, about 600 fL, about 610 fL, about 620 fL, about 630 fL, about 640 fL, about 650 fL, about 660 fL, about 670 fL, about 680 fL, about 690 fL, about 700 fL, about 710 fL, about 720 fL, about 730 fL, about 740 fL, about 750 fL, about 760 fL, about 770 fL, about 780 fL, about 790 fL, about 800 fL, about 810 fL, about 820 fL, about 830 fL, about 840 fL, about 850 fL, about 860 fL, about 870 fL, about 880 fL, about 890 fL, about 900 fL, about 910 fL, about 920 fL, about 930 fL, about 940 fL, about 950 fL, about 960 fL, about 970 fL, about 980 fL, about 990 fL, about 1 pL, about 10 pL, about 20 pL, about 30 pL, about 40 pL, about 50 pL, about pL, about 60 pL, about 70 pL, about 80 pL, about 90 pL, about 100 pL, about 200 pL, about 300 pL, about 400 pL, about 500 pL, about 600 pL, about 700 pL, about 800 pL, about 900 pL, about 999 pL (e.g., less than 1 nL), about 1 nL, or any amount between the listed amounts.

In certain embodiments, the atomized indicator fluid has a reactable surface area of at least about 1000 square centimeters per gram ($cm^2/g$), for example, at least about 2000 $cm^2/g$, or at least about 2500 $cm^2/g$. For example, the atomized indicator fluid can have a reactable surface area of at least about 1000 $cm^2/g$, about 1100 $cm^2/g$, about 1200 $cm^2/g$, about 1300 $cm^2/g$, about 1400 $cm^2/g$, about 1500 $cm^2/g$, about 1600 $cm^2/g$, about 1700 $cm^2/g$, about 1800 $cm^2/g$, about 1900 $cm^2/g$, about 2000 cm $cm^2/g$, about 2100 $cm^2/g$, about 2200 $cm^2/g$, about 2300 $cm^2/g$, about 2400 $cm^2/g$, about 2500 $cm^2/g$, about 2600 $cm^2/g$, about 2700 $cm^2/g$, about 2800 $cm^2/g$, about 2900 $cm^2/g$, about 3000 $cm^2/g$, about 3100 $cm^2/g$, about 3200 $cm^2/g$, about 3300 $cm^2/g$, about 3400 $cm^2/g$, about 3500 $cm^2/g$, about 3600 $cm^2/g$, about 3700 $cm^2/g$, about 3800 $cm^2/g$, about 3900 $cm^2/g$, about 4000 $cm^2/g$, about 4100 $cm^2/g$, about 4200 $cm^2/g$, about 4300 $cm^2/g$, about 4400 $cm^2/g$, about 4500 $cm^2/g$, about 4600 $cm^2/g$, about 4700 $cm^2/g$, about 4800 $cm^2/g$, about 4900 $cm^2/g$, about 5000 $cm^2/g$, or any amount between the listed values.

The systems described herein are amenable to detecting or analyzing one or more analytes present in the subject's breath in very small concentrations (e.g., analytes present in the subject's breath at a concentration about 500 parts per billion (ppb) or less). For example, the analytes can be present in the subject's breath at a concentration of about 1 ppb, about 5 ppb, about 10 ppb, about 20 ppb, about 30 ppb, about 40 ppb, about 50 ppb, about 60 ppb, about 70 ppb, about 80 ppb, about 90 ppb, about 100 ppb, about 110 ppb, about 120 ppb, about 130 ppb, about 140 ppb, about 150 ppb, about 160 ppb, about 170 ppb, about 180 ppb, about 190 ppb, about 200 ppb, about 210 ppb, about 220 ppb, about 230 ppb, about 240 ppb, about 250 ppb, about 260 ppb, about 270 ppb, about 280 ppb, about 290 ppb, about 300 ppb, about 310 ppb, about 320 ppb, about 330 ppb, about 340 ppb, about 350 ppb, about 360 ppb, about 370 ppb, about 380 ppb, about 390 ppb, about 400 ppb, about 410 ppb, about 420 ppb, about 430 ppb, about 440 ppb, about 450 ppb, about 460 ppb, about 470 ppb, about 480 ppb, about 490 ppb, or about 500 ppb.

In certain embodiments, the systems described herein include a storage vessel for storing the indicator fluid. In certain aspects, the vessel is in fluid communication with the nozzle such that the indicator fluid is transported from the storage vessel to the reaction chamber via the nozzle. In some examples, the storage vessel is in fluid communication with a system for atomizing the indicator fluid, and the system for atomizing the indicator fluid is in fluid communication with the nozzle. Thus, the indicator fluid is transported from the storage vessel to the system for atomizing the indicator fluid, and the atomized indicator fluid is delivered to the reaction chamber via the nozzle.

In certain embodiments, the systems described herein include a system for atomizing the indicator fluid or atomized version thereof. By way of example, the system for atomizing the indicator fluid is an inkjet nozzle, a piezoelectric drive actuator, a piezoelectric disc actuator, or an acoustic printing nozzle In the example of an inkjet nozzle, the system is configured to heat a liquid indicator fluid to provide a gas indicator fluid. The vapor pressure of the gas indicator fluid forces the gas indicator fluid through the inkjet nozzle. Upon exiting the inkjet nozzle, the gas indicator fluid is a mist of sub-nanoliter droplets described above. Optionally, the system for atomizing the indicator fluid can employ piezoelectric actuators to force the liquid indicator fluid through the nozzle, thus atomizing the indicator fluid. In some examples, the liquid indicator fluid is dispensed into the reaction chamber, and a piezoelectric substrate is employed to atomize the indicator fluid within the reaction chamber. In a further example, the indicator fluid is ultrasonically agitated in an acoustic inkjet nozzle to atomize the indicator fluid.

In certain embodiments, the system can detect a plurality of compounds in the subject's breath. For example, a plurality of indicator fluids can be employed to analyze a plurality of compounds found in a subject's breath in a single system and, optionally, in a single sample. Accordingly, a plurality of storage vessels and a plurality of nozzles, and optionally a plurality of atomizing systems, can be employed in concert (e.g., in a single sample) and/or individually (e.g., in multiple samples) to analyze the subject's breath.

In some non-limiting embodiments, the systems described herein include a closed system 100 as in the example of FIG. 1. The closed system 100 can include a liquid atomizer 110 (e.g., an ink jet cartridge), a receiving substrate 120, a supply spool 130 providing the receiving substrate 120, a take-up spool 140 connected to a motor 150 can gather the receiving substrate 120 after breath analysis, and a reaction chamber 160 wherein the indicator fluid can be reacted with the subject's breath. As shown in FIG. 1, the closed system 100 can be configured to continually analyze a subject's breath (e.g., for chronically ill patients), or the closed system 100 can be configured to intermittently analyze a sample of the subject's breath. Accordingly, the subject's breath can continuously flow into the closed system 100, or the subject's breath can be intermittently passed into the closed system 100 via a breath inlet 170. The take-up spool 140 and motor 150 can be activated to begin gathering the receiving substrate 120. As the receiving substrate 120 passes adjacent to the liquid atomizer 110 (e.g., at the reaction chamber 160), the indicator fluid (not visible) can be atomized and the droplets collected by the receiving substrate 120 in the reaction chamber 160. The receiving substrate 120 having the indicator fluid can then pass by an alternate breath inlet 180 to analyze the subject's breath. A chemical reaction (e.g., a color change reaction) can be analyzed and/or recorded by a human observer or any suitable analytical tool described above. Optionally, the liquid atomizer 110 is configured to provide the atomized indicator fluid into the reaction chamber 160, and the breath inlet 170 can be configured to deliver the subject's breath into the reaction chamber 160, such that the reaction occurs within the reaction chamber 160 and a reaction product subsequently falls onto the receiving substrate 120 on the receiving side of the receiving substrate. The reaction product collected by the receiving substrate 120 can be analyzed and/or recorded by a human observer or any suitable analytical tool described above.

Methods

Disclosed herein are methods of analyzing a subject's exhaled breath, including receiving the subject's breath in the reaction chamber; dispensing one or more indicator fluids into the reaction chamber; reacting the subject's breath with a plurality of droplets of the one or more indicator fluids to produce one or more reaction products on the receiving substrate; and detecting the presence or amount of one or more reaction products. In certain embodiments, dispensing the one or more indicator fluids into the reaction chamber occurs before the subject's breath is received by the system. In some examples, receiving the subject's breath and dispensing the one or more indicator fluids occurs substantially simultaneously. In some embodiments, the one or more indicator fluids are dispersed into the chamber after the subject's breath is received in the chamber.

In certain embodiments, the subject's breath is delivered to the reaction chamber by the breath inlet described above. Delivering the subject's breath into the reaction chamber optionally includes reducing the volume of the subject's breath in the sample reaching the reaction chamber. For example, delivering the subject's breath into the reaction chamber can include passing the subject's breath from the breath inlet to the reaction chamber via a reducing coupling. In some cases, the subject can deliver breath directly into the reaction chamber (e.g., the breath inlet is integrated into the reaction chamber, for example, in a disposable system designed for a single use by a single subject or a system designed for multiple uses by the same subject).

In certain embodiments, an atomized indicator fluid is dispensed into the reaction chamber. In some examples, atomizing the indicator fluid includes creating a plurality of sub-nanoliter droplets of the indicator fluid (e.g., the volume of the droplets is in the pL range and/or in the fL ranges described above). The atomized indicator fluid is then dispersed into the reaction chamber. In one embodiment, the atomized indicator fluid is reacted with the subject's breath at or near the center of the reaction chamber, such that the reaction product forms and optionally falls to a substrate. The atomized indicator fluid, however, can collect on the receiving substrate where it reacts with analytes in the subject's breath to form reaction products.

In certain embodiments, reacting the subject's breath with the indicator fluid provides a reaction product exhibiting a visible color change. For example, a visible color change can include a transparent colorless indicator fluid changing to a transparent, translucent, or opaque fluid having an identifiable color. Accordingly, the methods and systems described herein can be tailored to analyze specific compounds contained in the subject's breath based on the presence or amount of reaction product(s). In one non-limiting example, nitric oxide contained in an asthmatic patient's breath can be detected using a reagent designed to react with nitric oxide (e.g., 4,5-Diaminofluorescein diacetate (DAF-2), 2,3-Diaminonaphthalene (DAN), and/or a Greiss reagent) and the reaction product detected.

In certain embodiments, a plurality of indicator fluids can be employed to analyze a plurality of compounds found in a subject's breath in a single system and optionally in a single sample. Accordingly, a plurality of storage vessels, a plurality of nozzles, and optionally one or more atomizing systems can be employed in concert and/or individually to analyze the subject's breath. Thus, a plurality of reaction products can be detected to indicate the contents of the subject's breath.

In certain embodiments, detecting the contents of the subject's breath is performed by observing the visible color change of the reaction product. The visible color change is emphasized by the receiving substrate. For example, a reaction product that is a transparent, translucent, or opaque fluid having an identifiable color can be collected onto an opaque white receiving substrate. Accordingly, the opaque white receiving substrate can enhance the observable color of the reaction product, facilitating observation by a human observer or a sensor (e.g., a spectrophotometer, a camera, or a fluorescence spectrometer). In some cases, detecting the contents of the subject's breath is performed by detecting a chemical signature of the reaction product. For example, the reaction product can be a compound detectable by a chemical sensor (e.g., a litmus strip). Accordingly, chemically detecting the reaction product can indicate the contents of the subject's breath. In some cases, the reaction product can exhibit an exothermic reaction or an endothermic reaction. Thus, thermally detecting the reaction product, for example, by using an infrared sensor, can indicate the contents of the subject's breath.

EXAMPLE ASPECTS OF VARIOUS EMBODIMENTS

Example aspect 1 is a system for analyzing a subject's breath, comprising: a) a breath inlet configured to receive the subject's breath; b) a reaction chamber comprising a receiving substrate, wherein the receiving substrate is positioned inside the reaction chamber and is configured to receive a reaction product from a reaction between the subject's breath and an indicator fluid, wherein the reaction chamber is configured to receive the subject's breath through the breath inlet; c) a nozzle comprising a delivery end positioned at or within the reaction chamber and a supply end positioned outside of the reaction chamber, wherein the nozzle is configured to receive an indicator fluid at its supply end and to dispense the indicator fluid into the reaction chamber; and d) an indicator fluid delivery device in fluid communication with the supply end of the nozzle.

Example aspect 2 is the system of any subsequent or preceding example aspect illustration, further comprising an indicator fluid storage vessel in fluid communication with the indicator fluid delivery device.

Example aspect 3 is the system of any subsequent or preceding example aspect illustration, wherein the system further comprises a sensor configured to analyze the reaction product.

Example aspect 4 is the system of any subsequent or preceding example aspect illustration, wherein the sensor comprises an optical sensor, a chemical sensor, and a human observer.

Example aspect 5 is the system of any subsequent or preceding example aspect illustration, wherein the reaction chamber comprises a chamber volume of up to about 10 milliliters.

Example aspect 6 is the system of any subsequent or preceding example aspect illustration, wherein the chamber volume is up to about 5 milliliters.

Example aspect 7 is the system of any subsequent or preceding example aspect illustration, wherein the nozzle is configured to dispense the indicator fluid as an atomized fluid, an aerosol, or a liquid.

Example aspect 8 is the system of any subsequent or preceding example aspect illustration, wherein the nozzle is configured to dispense the indicator fluid as an atomized fluid comprising a plurality of droplets.

Example aspect 9 is the system of any subsequent or preceding example aspect illustration, wherein each droplet in the plurality of droplets comprises an indicator fluid volume of less than one nanoliter.

Example aspect 10 is the system of any subsequent or preceding example aspect illustration, wherein each droplet in the plurality of droplets comprises a volume less than one picoliter.

Example aspect 11 is the system of any subsequent or preceding example aspect illustration, wherein the nozzle is configured to dispense the indicator fluid as a liquid and wherein the reaction chamber comprises a piezoelectric disc actuator configured to converted the liquid into a plurality of droplets.

Example aspect 12 is the system of any subsequent or preceding example aspect illustration, wherein the plurality of droplets of indicator fluid comprises a reactable surface area of at least 2000 square centimeters per gram of indicator fluid.

Example aspect 13 is the system of any subsequent or preceding example aspect illustration, wherein the plurality of droplets of indicator fluid comprise a reactable surface area of at least 2500 square centimeters per gram of indicator fluid.

Example aspect 14 is the system of any subsequent or preceding example aspect illustration, wherein the nozzle is configured to dispense up to about 100 microliters of the indicator fluid into the reaction chamber for each breath to be analyzed.

Example aspect 15 is the system of any subsequent or preceding example aspect illustration, wherein the nozzle is configured to provide up to dispense about 50 microliters of the indicator fluid into the reaction chamber for each breath to be analyzed.

Example aspect 16 is the system of any subsequent or preceding example aspect illustration, wherein the reaction chamber is configured to receive up to about 100 milliliters of the subject's breath.

Example aspect 17 is the system of any subsequent or preceding example aspect illustration, wherein the reaction chamber is configured to receive up to about 50 milliliters of the subject's breath.

Example aspect 18 is the system of any subsequent or preceding example aspect illustration, wherein the reaction chamber is configured to receive up to about 8 liters per minute of the subject's breath.

Example aspect 19 is the system of any subsequent or preceding example aspect illustration, wherein the reaction chamber is configured to receive up to about 5 liters per minute of the subject's breath.

Example aspect 20 is the system of any subsequent or preceding example aspect illustration, wherein the reaction chamber is configured to receive up to about 1 liter per minute of the subject's breath.

Example aspect 21 is the system of any subsequent or preceding example aspect illustration, wherein the reaction product comprises a detectable change in color.

Example aspect 22 is the system of any subsequent or preceding example aspect illustration, wherein the receiving substrate is configured to optically enhance the reaction product.

Example aspect 23 is method of analyzing one or more analytes in a subject's breath using the system of any subsequent or preceding example aspect illustration, comprising: a) receiving the subject's breath in the reaction chamber; b) dispensing one or more indicator fluids into the reaction chamber; c) reacting the subject's breath with a plurality of droplet of the one or more indicator fluids to produce one or more reaction products on the receiving substrate; and d) detecting a presence or amount of one or more reaction products.

Example aspect 24 is the system of any subsequent or preceding example aspect, wherein the detecting comprises optical or chemical detection.

Examples

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure.

In one non-limiting example, a subject having asthma and/or COPD can exhale elevated levels of nitric oxide when compared to a control subject without asthma or COPD. Additionally, amounts of nitric oxide in the subject's breath can indicate effective disease management (e.g., the effectiveness of inhaled steroid medications). The concentration of the nitric oxide in the subject's breath can be very low, for example, about 50 ppb or less. Detection of a compound having such a low concentration in a subject's breath can require a substantial amount of the subject's breath (e.g., up to about 600 mL) using conventional systems. However, such a substantial amount of the subject's breath can be difficult for certain subjects with compromised pulmonary function or limited lung capacity to deliver. Thus, as described herein, by increasing the surface area of the indicator fluid or atomized version thereof, the system requires significantly less of the subject's breath (e.g., about 50 mL, about 10 mL, about 5 mL, or less), and can detect certain compounds, for example, nitric oxide, in very low concentrations (e.g., about 10 ppb, about 5 ppb, or less).

An indicator fluid as described above (e.g., DAF-2, DAN, and/or a Greiss reagent) is atomized and dispensed into the reaction chamber. The subject then exhales into the reaction chamber, wherein nitric oxide contained in the subject's breath reacts with the atomized indicator fluid, providing a reaction product having a translucent yellow appearance. The reaction product falls onto the receiving substrate (e.g., by gravity) wherein it is observed by a human observer and/or detected by an optical sensor. The selected substrate is opaque and white so as to enhance the visibility of the translucent yellow reaction product, facilitating detection.

Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

When introducing elements of the present disclosure or the embodiment(s) thereof, the articles a, an, the, and said are intended to mean that there are one or more of the elements. The terms comprising, including, and having are intended to be inclusive and mean that there may be additional elements other than the listed elements. It is understood that aspects and embodiments of the disclosure described herein include consisting of and/or consisting essentially of aspects and embodiments.

The term and/or, when used in a list of two or more items, means that any one of the listed items can be employed by itself or in combination with any one or more of the listed items. For example, the expression A and/or B is intended to mean either or both of A and B, i.e. A alone, B alone, or A and B in combination. The expression A, B and/or C is intended to mean A alone, B alone, C alone, A and B in combination, A and C in combination, B and C in combination or A, B, and C in combination.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a droplet is a self-contained volume of a first medium dispersed, suspended, or otherwise included in a second medium. Generally, the first medium of the droplet is a liquid and the second medium is either a liquid or a gas, though it need not be. The droplet may be homogeneous or heterogeneous (i.e., include other materials within the droplet such as solid particles, gas bubbles, miscible liquids, immiscible liquids, cells, cellular material, biological elements, liposomes, medicaments, therapeutic elements, marker molecules, or the like).

The term embodiment and like terms are intended to refer broadly to all of the subject matter of this disclosure and the claims below. Statements containing these terms should be understood not to limit the subject matter described herein or to limit the meaning or scope of the claims below.

The foregoing description of the embodiments, including illustrated embodiments, is presented only for the purpose of illustration and description and is not intended to be exhaustive or limiting to the precise forms disclosed. Numerous modifications, adaptations, and uses thereof will be apparent to those skilled in the art.

What is claimed is:

1. A system for analyzing a subject's breath, comprising:
   a breath inlet configured to receive the subject's breath;
   a reaction chamber, wherein the reaction chamber is configured to receive the subject's breath through the breath inlet;
   a receiving substrate, wherein the receiving substrate comprises a receiving side that is positioned to face inside the reaction chamber, and wherein the receiving side of the receiving substrate is configured to receive a reaction product from a reaction between the subject's breath and an indicator fluid, wherein the receiving substrate is movable and configured to carry the reaction product on the receiving side out of the reaction chamber;
   a nozzle comprising a delivery end positioned at or within the reaction chamber and a supply end positioned outside of the reaction chamber, wherein the nozzle is configured to receive the indicator fluid at its supply end and to dispense the indicator fluid into the reaction chamber; and
   an indicator fluid delivery device in fluid communication with the supply end of the nozzle.

2. The system of claim 1, further comprising an indicator fluid storage vessel in fluid communication with the indicator fluid delivery device.

3. The system of claim 1, wherein the system further comprises a sensor configured to analyze the reaction product.

4. The system of claim 3, wherein the sensor comprises an optical sensor, a chemical sensor, and a human observer.

5. The system of claim 1, wherein the reaction chamber comprises a chamber volume of 1 milliliter to 10 milliliters.

6. The system of claim 1, wherein the receiving substrate is movable between a first position in the reaction chamber and a second position adjacent to a sensor configured to analyze the reaction product.

7. The system of claim 1, wherein the nozzle is configured to dispense the indicator fluid as a liquid.

8. The system of claim 1, wherein the nozzle is configured to dispense the indicator fluid as an atomized fluid comprising a plurality of droplets.

9. The system of claim 8, wherein each droplet in the plurality of droplets comprises an indicator fluid volume of less than one nanoliter.

10. The system of claim 9, wherein each droplet in the plurality of droplets comprises a volume less than one picoliter.

11. The system of claim 7, further comprising a piezoelectric disc actuator positioned in the reaction chamber and configured to convert the liquid into a plurality of droplets.

12. The system of claim 8, wherein the plurality of droplets of indicator fluid comprises a reactable surface area of at least 2000 square centimeters per gram of indicator fluid.

13. The system of claim 1, wherein the breath inlet includes a valve configured to enclose the subject's breath within the reaction chamber.

14. The system of claim 1, wherein the nozzle is configured to dispense up to 100 microliters of the indicator fluid into the reaction chamber for each breath to be analyzed.

15. The system of claim 1, wherein the breath inlet is configured to control or limit a volume of the subject's breath that enters the reaction chamber.

16. The system of claim 1, wherein the reaction chamber is configured to receive up to 100 milliliters of the subject's breath or up to 8 liters per minute of the subject's breath.

17. The system of claim 1, wherein the receiving substrate comprises a tape or a slide.

18. The system of claim 17, wherein the tape is a transparent tape, a translucent tape, or an opaque tape, or wherein the slide is a transparent slide, a translucent slide or an opaque slide.

19. The system of claim 1, wherein the receiving substrate further comprises a non-receiving side that is positioned to face away from the reaction chamber.

20. The system of claim 1, further comprising a supply spool and a collection spool, wherein the receiving substrate comprises a web of material extending between the supply spool and the collection spool and passing through the reaction chamber.

21. The system of claim 1, wherein the reaction product comprises a detectable change in color.

22. The system of claim 1, wherein the receiving substrate is white or transparent or wherein the reaction chamber includes an opaque white portion or a transparent portion.

23. A method of analyzing one or more analytes in a subject's breath using the system of claim 1, comprising:
   receiving the subject's breath in the reaction chamber;
   dispensing one or more indicator fluids into the reaction chamber;
   reacting the subject's breath with a plurality of droplets of the one or more indicator fluids to produce one or more reaction products on the receiving substrate; and
   detecting a presence or amount of the one or more reaction products.

24. The method of claim 23, wherein the detecting comprises optical or chemical detection.

* * * * *